United States Patent [19]

Bernstein et al.

[11] 4,221,725
[45] Sep. 9, 1980

[54] STEROID DERIVATIVES AND THEIR USE IN RADIOIMMUNOASSAYS

[75] Inventors: Jack Bernstein, News Brunswick; Ravi K. Varma, Belle Mead, both of N.J.; B. Richard Vogt, Yardley, Pa.; Frank L. Weisenborn, Titusville, N.J.

[73] Assignee: E. R. Squibb & Sons, Inc., Princeton, N.J.

[21] Appl. No.: 4,092

[22] Filed: Jan. 17, 1979

Related U.S. Application Data

[60] Division of Ser. No. 901,952, May 1, 1978, which is a continuation-in-part of Ser. No. 824,016, Aug. 12, 1977, abandoned.

[51] Int. Cl.$^2$ ............................................. C07D 309/06
[52] U.S. Cl. ........................... 260/345.8 R; 260/397.1; 424/1; 424/238; 562/471
[58] Field of Search ................... 260/345.9 R, 345.8 R

[56] References Cited

U.S. PATENT DOCUMENTS

| | | | |
|---|---|---|---|
| 2,792,418 | 5/1957 | Druey et al. | 260/345.9 R |
| 3,810,886 | 5/1974 | Rutner et al. | 260/239.57 |
| 3,855,208 | 12/1974 | Rutner et al. | 260/239.57 |
| 3,925,355 | 12/1975 | Piasio et al. | 424/182 |
| 3,954,739 | 5/1976 | Wilkinson | 260/239.57 |
| 3,981,982 | 9/1976 | Oslapas et al. | 424/1.5 |
| 4,021,535 | 5/1977 | Polito | 424/1 |

FOREIGN PATENT DOCUMENTS 839606 7/1976 Belgium.

OTHER PUBLICATIONS

Mndzhoyan et al., Chem. Abstracts, 79, 9174p (1973).
Beatmann et al., Tetrahedron Letters, No. 25, pp. 2101–2106 (1969).
Smith et al., JACS, 72, 1877 (1950).
Smith et al., J. Org. Chem., 26, 3856 (1961).
Pandya et al., J. Indian Chem. Soc., 34, 231 (1957).

*Primary Examiner*—Nickey Chan
*Attorney, Agent, or Firm*—Lawrence S. Levinson; Donald J. Barrack

[57] ABSTRACT

Radiolabeled steroid derivatives having the formula

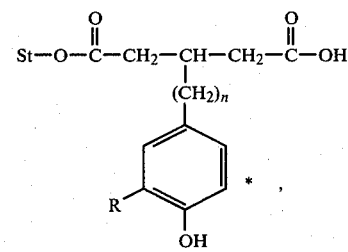

wherein St is des-hydroxy steroid moiety of (i) a hydroxy steroid intended for radioimmunoassay or (ii) a hydroxy containing derivative of a steroid intended for radioimmunoassay, said derivative having a strong affinity for the antibodies of the steroid intended for radioimmunoassay; R is hydrogen or alkyl of 1 to 3 carbon atoms; n is 0, 1, 2, 3 or 4 and the asterisk (*) indicates tagging with a radioisotope, are useful as tracers in radioimmunoassays.

7 Claims, No Drawings

STEROID DERIVATIVES AND THEIR USE IN RADIOIMMUNOASSAYS

This is a division, of application Ser. No. 901,952, filed May 1, 1978 which is a continuation-in-part of application Ser. No. 824,016, filed Aug. 12, 1977 and now abandoned.

BACKGROUND OF THE INVENTION

The measurement of various substances by the use of radioimmunoassay techniques has achieved widespread acceptance in recent years. Yalow and Berson, *In Vitro Procedures With Radioisotopes In Medicine,* International Atomic Energy Agency, Vienna (1970) pgs. 455 et seq., express the principle of radioimmunoassay in the following terms:

"Unlabelled antigen in unknown samples competes against labelled antigen ("tracer") for binding to antibody and thereby diminishes the binding of labelled antigen. The degree of competitive inhibition observed in unknown samples is compared with that obtained in known standard solutions for determination of concentration of antigen in unknowns."

Radioimmunoassay tests require a specific antibody, a radioisotope-labeled (hereinafter referred to as "radiolabeled") antigen, a pure sample of the antigen to be measured to serve as a reference standard, and means for the separation of free antigen from antibody-bound antigen. Radioimmunoassays follow the basic principle of saturation analysis, i.e., competition between labeled and unlabeled antigen for a fixed number of antibody binding sites.

When radiolabeled antigen, unlabeled antigen, and antibody are brought together, the amount of radiolabeled antigen bound to antibody and the amount of radiolabeled antigen remaining unbound (free) has a direct relationship to the amount of unlabeled antigen present when a given amount of antibody is present. Thus, by using a constant amount of antibody and radiolabeled antigen, and using known concentrations of unlabeled antigen, a standard (calibration) curve can be plotted showing antigen concentration versus the amount of radiolabeled antigen bound or versus radiolabeled antigen unbound, or versus a ratio of the two measurements. The concentration of antigen in an unknown sample can be read from the standard curve by determining the amount of bound or free radiolabeled antigen (or ratio of the two measurements) resulting when the unknown sample is mixed with the amount of radiolabeled antigen and antibody used to prepare the curve. In all radioimmunoassay procedures it is necessary to provide means for separating the bound from the free labeled tracer material. Many widely varied procedures have been developed and used; exemplary procedures are electrophoresis; chromatography; ion exchange; adsorption to dextran coated charcoal, talc, or cellulose; and a number of solid-phase antibody techniques.

The term "antigen", as used in the field of radioimmunoassays, may cover substances of limited immunogenicity (ability to generate antibodies). In those cases where the substance to be measured is of limited immunogenicity, the substance can be coupled with an immunogenic carrier, usually a protein, to increase its immunogenicity. A substance that is nonimmunogenic, but acquires immunogenicity when linked with a carrier is referred to as a "hapten".

Radioimmunoassay techniques have been used to determine the concentration in body fluids of various endogenous and exogenous steroids. In the development of radioimmunoassays for the various steroids, the preparation of a radiolabeled antigen is of primary concern. Possible radioisotope labels are tritium, carbon-14, iodine-125, iodine-131, and others. However, because tritium and carbon-14 must be counted by liquid scintillation (a time-consuming and expensive process), iodine-125 and iodine-131 are more desirable. For reasons well-recognized in the art (e.g., half-life, radiation hazard, counting efficiency and others) iodine-125 has become the radioisotope of choice for use in steroid radioimmunoassays.

The chemical structure of steroids is such that it is generally not possible to radioiodinate them directly. It is necessary, therefore, to utilize as a precursor of the radiolabeled antigen a derivative of the steroid to be assayed which is readily iodinated. In choosing or developing such a derivative, the primary concern is the affinity of the derivative for the antibodies of the steroid to be assayed; the affinity of the derivative for the antibodies should, of course, be as close to the affinity of the steroid for the antibodies as possible.

BRIEF DESCRIPTION OF THE INVENTION

Compounds having the formula

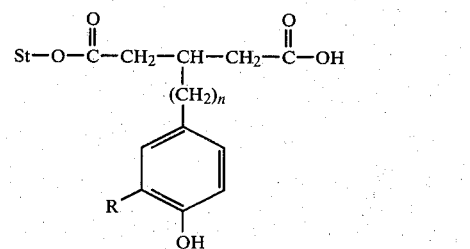

are readily tagged with a radioisotope and can be used (when radiolabeled) as a tracer in radioimmunoassay procedures for the determination of steroid levels in a body fluid. In formula I, and throughout the specification, R is hydrogen or an alkyl group of 1 to 3 carbon atoms; n is 0, 1, 2, 3 or 4 and St is a des-hydroxy steroid moiety of (i) a hydroxy steroid intended for radioimmunoassay or (ii) a hydroxy containing derivative of a steroid intended for radioimmunoassay, said derivative having a strong affinity for the antibodies of the steroid intended for radioimmunoassay.

Exemplary of hydroxy steroids intended for radioimmunoassay which may be modified structurally as shown in formula I are: cholesterol, cortisol, cortisone, corticosterone, prednisolone, methylprednisolone, triamcinolone, betamethasone, dexamethasone, triamcinolone acetonide, betamethasone valerate, halcinonide, aldosterone, estrone, estradiol, estriol, testosterone, 19-nortestosterone, methyltestosterone, and pregnenolone. Exemplary of hydroxy containing derivatives of a steroid intended for radioimmunoassay (which derivatives have a strong affinity for the antibodies of the steroid intended for radioimmunoassay) are digoxigenin, digitoxigenin and 11α-hydroxyprogesterone.

DETAILED DESCRIPTION OF THE INVENTION

The steroids of formula I are prepared from the precursor hydroxy steroid having the formula St-OH and a glutaric anhydride derivative having the formula

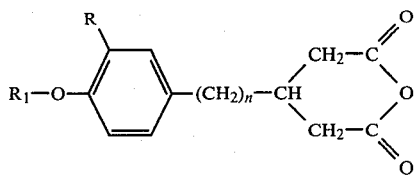

In formula II, and throughout the specification, $R_1$ is an alkanoyl group having 2 to 6 carbon atoms, acetyl being the preferred group.

The anhydrides of formula II are novel compounds, and as such constitute an integral part of this invention. They can be prepared by first reacting a 4-methoxyphenyl aliphatic aldehyde having the formula

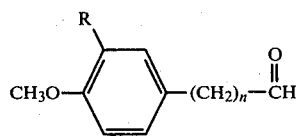

with at least 2 molar equivalents of cyanoacetic acid in the presence of a base (e.g., sodium hydroxide) to yield, on acid hydrolysis, a compound having the formula

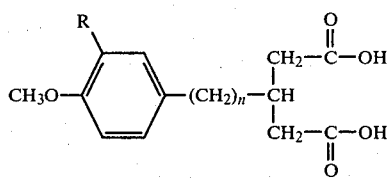

An alternative preparation for the compound of formula IV wherein n is 0 and R is hydrogen, i.e., 3-(4-methoxyphenyl)glutaric acid, is disclosed by Smith et al., *J.A.C.S.*, 72, 1877 (1950). In that procedure, anisaldehyde is condensed with ethyl acetoacetate in the presence of piperidine to give ethyl anisal-bis-acetoacetate. Cleavage of this product to give the desired 3-(4-methoxyphenyl)glutaric acid can be accomplished with boiling alcoholic sodium hydroxide solution.

Demethylation of the glutaric acid derivatives of formula IV results in glutaric acid derivatives having the formula

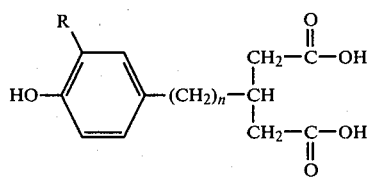

and can be accomplished by following one of the several procedures known in the art for the demethylation of aryl methyl esters. One such procedure, described by Feutrill et al., *Aust. J. Chem.*, 25, 1719 (1972), involves the treatment of the aryl methyl ether with thioethoxide ion (readily prepared in situ from ethanethiol and sodium hydride) in a polar aprotic solvent, preferably dimethylformamide.

The phenolic hydroxy group of a compound of formula V can be protected with an alkanoyl group using art-recognized procedures. One such procedure comprises reacting the glutaric acid derivative with the appropriate acid anhydride (acetic anhydride is preferred). The preferred method of preparing a glutaric anhydride derivative of formula II from the glutaric acid derivative of formula V is to combine the conversion of the acid to anhydride and the protection of the phenolic hydroxy group into a single step. When the $R_1$ protecting group is acetyl, this would involve heating a glutaric acid derivative of formula V in acetic anhydride.

The reaction of a steroid precursor having the formula St-OH and a glutaric anhydride derivative of formula II to yield a steroid having the formula

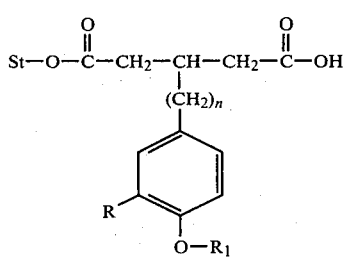

can be run in the presence of an organic base. Exemplary organic bases are nitrogen containing heterocyclics, e.g., pyridine, and tertiary amines, e.g., triethylamine. The reaction will preferably be run at an elevated temperature.

In those instances wherein the steroid precursor has more than one hydroxy substituent, it will be possible to monoacylate the steroid with a glutaric anhydride derivative of formula II because of the varying reactivities of the steroids hydroxyl substituents. If it is desirable to acylate a hydroxy substituent other than the most reactive one, conventional blocking techniques should be used to protect the more reactive substituents.

Removal of the phenolic hydroxyl protecting group in a compound of formula VI yields the corresponding product of formula I.

The compounds of formula I can be labeled ("tagged") with a radioisotope, preferably iodine-125 or iodine-131, and most preferably iodine-125, using procedures well known in the art, to yield a radiolabeled hapten having the formula

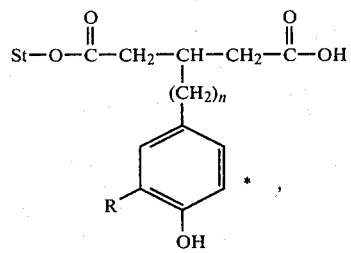

The asterik (*) in formula VII indicates tagging with a radioisotope. Exemplary of the methods known in the art is the method of Hunter and Greenwood; see *Nature*, 194:495 (1962). The radiolabeled compounds of formula VII form an integral part of this invention.

The radiolabeled compounds of formula VII can be used as tracers in radioimmunoassay procedures following the general principles set forth in the Background of the Invention, supra. Exemplary detailed procedures are described in Jaffe et al., "Methods of Hormone Radioimmunoassay", Academic Press, New York (1974) and Berson et al., "Methods in Investigative and Diagnostic Endocrinology", Vol. 3 on "Steroid Hormones", North Holland, Amsterdam (1975). The radiolabeled compounds of this invention are particularly useful as reagents in the automated radioimmunoassay system of Brooker et al. disclosed in U.S. Pat. No. 4,022,577 issued May 10, 1977.

The following examples are specific embodiments of this invention.

EXAMPLE 1

$(3\beta,5\beta,12\beta)$-3-[4-Carboxy-3-(4-hydroxyphenyl)-1-oxobutoxy]-12,14-dihydroxycard-20(22)-enolide (A) 3-(4-Methoxyphenyl)glutaric acid A mixture of p-anisaldehyde (27.2 g), ethyl acetoacetate (52.1 g) and piperidine (4 ml) in 95% ethanol (10 ml) is stirred at room temperature for 5.0 hours while a solid forms. The solid is isolated by filtration, washed with 25% ethanol and crystallized from 95% ethanol to afford ethyl, 2,2'-(4-methoxybenzal)-bis-acetoacetate (31.4 g), melting point 138°–141° C. The filtrate on dilution with an equal amount of water gives a solid which is crystallized from 95% ethanol to afford another crop of material (8.5 g), melting point 137°–142° C.

A mixture of ethyl 2,2'-(4-methoxybenzal)-bis-acetoacetate (30 g), ethanol (450 ml) and 50% sodium hydroxide (450 g) is refluxed vigorously for 1.0 hour. Water (150 ml) is added and most of the ethanol is removed by distillation in vacuo. The concentrate is acidified with concentrated hydrochloric acid and is extracted with ethyl acetate. The ethyl acetate solution is washed with brine, dried, evaporated and the residue is crystallized from benzene-methanol to afford 3.3 g of 3-(4-methoxyphenyl)glutaric acid, melting point 147°–150° C.

(B) 3-(4-Hydroxyphenyl)glutaric acid

To a stirred suspension of 57% sodium hydride-paraffin (6.45 g), in dry dimethylformamide (70 ml) is slowly added ethanethiol (11.89 ml) in dry dimethylformamide (20 ml). After stirring the resultant slurry for 15 minutes, a solution of 3-(4-methoxyphenyl)glutaric acid (3.0 g) in dry dimethylformamide (20 ml) is added. The slurry is heated in a bath at 165° C. for 5.0 hours and most of the solvent is removed by distillation in vacuo. The residue is diluted with water, acidified with concentrated hydrochloric acid and extracted twice with ether (the extracts are discarded). The solution is saturated with sodium chloride and extracted with ethyl acetate. The ethyl acetate solution is washed once with brine, dried and the residue crystallized from chloroform-hexane to afford 2.3 g of 3-(4-hydroxyphenyl)-glutaric acid, melting point 168°–170° C.

(C) 3-(4-Acetyloxphenyl)glutaric anhydride

A solution of 3-(4-hydroxyphenyl)glutaric acid (800 mg) in acetic anhydride (15 ml) is heated at 100° C. for 2.5 hours and evaporated to dryness in vacuo. The residual solid is crystallized from chloroform-hexane to afford 600 mg of 3-(4-acetyloxyphenyl)glutaric anhydride, melting point 140°–143° C.

12$\beta$-(Acetyloxy)-(3$\beta$,5$\beta$)-3-[4-carboxy-3-[4-(acetyloxy)-phenyl]-1-oxobutoxy]-14-hydroxycard-20(22)-enolide A solution of digoxigenin-12-acetate (130 mg) and 3-(4-acetyloxyphenyl)glutaric anhydride (286 mg) in dry pyridine (4.0 ml) is heated under nitrogen in a bath at 120° C. for 12 hours. Water (0.5 ml) is added and after 5 minutes the mixture is evaporated in vacuo. The residue is dissolved in chloroform, washed with 10% hydrochloric acid and brine, dried and evaporated. This residue is subjected to preparative thin-layer chromatography (tlc) on a silica gel plate (2.0×200×200 mm) using chloroform-methanol (9:1) for development to afford 110 mg of the title compound as an amorphous solid, melting point 118°–135° C.

(E) $(3\beta,5\beta,12\beta)$-3-[4-Carboxy-3-(4-hydroxyphenyl)-1-oxobutoxy]-12,14-dihydroxycard-20(22)-enolide To a solution of 12$\beta$-(acetyloxy)-(3$\beta$,5$\beta$)-3-[4-carboxy-3-[4-(acetyloxy)phenyl]-1-oxobutoxy]-14-hydroxycard-20(22)-enolide (68 mg) in methanol (3.0 ml) is added a solution of potassium carbonate (83 mg) in water (1.0 ml) and the mixture is stirred at room temperature for 2.5 hours. The solution is then acidified with 5% hydrochloric acid and the methanol is evaporated in vacuo. The residue is diluted with water (10 ml) and extracted with ethyl acetate. The ethyl acetate solution is washed with brine, dried over anhydrous magnesium sulfate, evaporated and the residue subjected to preparative tlc on silica gel plates (1×200×200 mm) using chloroform-methanol (3:1) for development to afford 22 mg of the title compound as an amorphous solid, melting point 110°–118° C. (melting completely to liquid at 144° C.).

EXAMPLE 2

$(3\beta,5\beta,12\beta)$-3-[4-Carboxy-3-[(4-hydroxyphenyl)methyl]-1-oxobutoxy]-12,14-dihydroxycard-20(22)-enolide (A) 3-[(4-Methoxyphenyl)methyl]glutaric acid To a solution of cyanoacetic acid (3.57 g), in water (20 ml) is added a solution of sodium hydroxide (2.08 g) in water (20 ml). The solution is diluted with glyme (70 ml), 4-methoxyphenyl acetaldehyde (3.0 g) is added and the mixture is left at room temperature for 6.0 hours. The glyme is evaporated in vacuo, and the residue is mixed with 10% hydrochloric acid (200 ml) and refluxed for 6.0 hours. After cooling, the mixture is extracted with ethyl acetate. The ethyl acetate extract is washed once with brine, dried, evaporated and the residue subjected to chromatography on a column of silica gel using chloroform-ethyl acetate mixtures for elution to afford 2.2 g of 3-[(4-methoxyphenyl)methyl]glutaric acid. Crystallization from a benzene-ethyl acetate-hexane mixture gives a specimen having a melting point 109°–110° C.

(B) 3-[(4-Hydroxyphenyl)methyl]glutaric acid

To a stirred suspension of 57% sodium hydride-paraffin (1.4 g) in dry dimethylformamide (30 ml) is added dropwise a solution of ethanethiol (4.0 ml) in dry dimethylformamide (10 ml). After 15 minutes, a solution of 3-[(4-methoxyphenyl)methyl]glutaric acid (800 mg) in dry dimethylformamide (20 ml) is added. The resulting slurry is heated in a bath at 165° C. for 20 hours and evaporated in vacuo. The residue is acidified with 20% hydrochloric acid, extracted with ether and the extracts are discarded. The aqueous solution is saturated with salt and extracted with ethyl acetate. The extracts are combined, washed once with brine, dried, evaporated and the residue crystallized from a mixture of ethyl acetate-chloroform-hexane to give 600 mg of 3-[(4-hydroxyphenyl)methyl]glutaric acid, melting point 117°–119° C.

(C) 3-[[(4-Acetyloxy)pheyl]methyl]glutaric anhydride

3-[(4-Hydroxyphenyl)methyl]glutaric acid (500 mg in acetic anhydride (15 ml) is heated in a bath at 120° C. for 2 hours. The solution is then evaporated to dryness in vacuo and the residue triturated with chloroform-hexane to afford 490 mg of the title compound, melting point 88°–89° C.

(D) 12β-(Acetyloxy)-(3β,5β)-3-[4-carboxy-3-[[4-acetyloxy)-phenyl]methyl]-1-oxobutoxy]-14-hydroxy-card-20(22)-enolide A solution of digoxigenin-12-acetate (216 mg) and 3-[[(4-acetyloxy)pnehyl]methyl]glutaric anhydride (500 mg) in dry pyridine (6.0 ml) is refluxed for 20 hours. Most of the pyridine is removed by distillation in vacuo and the residue is diluted with water (20 ml) and acidified with concentrated hydrochloric acid. The mixture is extracted with ethyl acetate, the extract washed twice with small amounts of brine, dried, evaporated and the residue subjected to preparative thin-layer chromatography (as in Example 1D) to isolate 323 mg of 12β-(acetyloxy)-(3β,5β)-3-[4-carboxy-3-[[4-(acetyloxy)-phenyl]methyl]-1-oxobutoxy]-14-hydroxycard-20(22)-enolide, melting point 70°–79° C.

(E) (3β,5β,12β)-[4-Carboxy-3-[(4-hydroxyphenyl)-methyl]-1-oxobutoxy]-12,14-dihydroxycard-20(22)-enolide A mixture of 12β-(acetyloxy)-(3β,5β)-3-[4-carboxy-3-[[4-(acetyloxy)phenyl]methyl]-1-oxobutoxy]-14-hydroxycard-20(22)-enolide (160 mg), methanol (20 ml), water (7.0 ml) and potassium carbonate (207 mg) is stirred at 15° C. for 2.5 hours. The mixture is acidified with concentrated hydrochloric acid and most of the methanol is evaporated in vacuo at room temperature. The concentrate is extracted with ethyl acetate, the extract washed with small amounts of brine, dried (MgSO₄anhydrous) evaporated and the residue subjected to a preparative thin-layer chromatography on silica gel plates (as in Example 1E) to afford 55 mg of (3β,5β,12β)-[4-carboxy-3-[(4-hydroxyphenyl)methyl]-1-oxobutoxy-12,14-dihydroxycard-20(22)-enolide, melting point 155°–165° C.

EXAMPLE 3

(3β,5β,12β)-3-[[3-(Carboxymethyl)-5-(4-hydroxyphenyl)-1-oxopentyl]oxy]-12,14-dihydroxycard-20(22)-enolide (A) 3-[2-(4-Methoxyphenyl)ethyl]glutaric acid To a solution of cyanoacetic acid (850 mg) in water (5.0 ml) is added a solution of sodium hydroxide (440 mg) in water (10 ml). The solution is diluted with glyme (15 ml) and 3-(4-methoxyphenyl)propionaldehyde (820 mg) is added. The solution is kept at room temperature for 10 hours and then evaporated to remove the glyme. To the residue is added 10% hydrochloric acid (50 ml) and the mixture is thereafter refluxed for 6 hours with stirring. It is then cooled and extracted with ethyl acetate. The extract is washed with brine, dried over anhydrous magnesium sulfate and evaporated. The residue is subjected to chromatography over silica gel (15 g) to isolate in chloroformethyl acetate (80/20) fraction, 600 mg of the title compound. Crystallization from ethyl acetate-benzene gives a specimen having a melting point of 98°–100° C.

(B) 3-[2-(4-Hydroxyphenyl)ethyl]glutaric acid

To a suspension of 57% sodium hydride-paraffin (2.2 g) in dry dimethylformamide (70 ml) in an atmosphere of nitrogen is slowly added ethanethiol (4.0 ml). The mixture is stirred at room temperature until a clear solution results. To this solution is added a solution of 3-[2-(4-methoxyphenyl)ethyl]-glutaric acid (1.2 g) in dry dimethylformamide (10 ml) and the mixture is heated with stirring in a bath at 165° C. for 6.0 hours. The mixture is then evaporated to dryness in vacuo and the resulting residue is dissolved in water (50 ml), extracted with ether (two 50 ml portions) and the ether extract is discarded. The aqueous solution is acidified with concentrated hydrochloric acid and extracted with ethyl acetate. The ethyl acetate solution is washed with brine, dried with anhydrous magnesium sulfate, and evaporated to a residue. Crystallization of this from chloroform-hexane affords 1.0 g of the title compound, melting point 142°–144° C.

(C) 3-[2-[4-(Acetyloxy)phenyl]ethyl]glutaric anhydride

A solution of 3-[2-(4-hydroxyphenyl)ethyl]glutaric acid (600 mg) in acetic anhydride (15 ml) is heated in a bath at 120° C. for 2.0 hours. It is evaporated in vacuo and the residue is crystallized from dichloromethane-hexane to afford 495 mg of 3-[2-[4-(acetyloxy)phenyl]ethyl]glutaric anhydride, melting point 97°–99° C.

(D) 12β-(Acetyloxy)-(3β,5β)-3-[[5-[4-(acetyloxy)-phenyl]-3-(carboxymethyl)-1-oxopentyl]oxy]card-20(22)-enolide A solution of digoxigenin-12-acetate (220 mg) and 3-[2-[4-(acetyloxy)phenyl]ethyl]glutaric anhydride (470 mg) in dry pyridine (8.0 ml) is refluxed for 20 hours. The pyridine is evaporated in vacuo, the residue diluted with water (25 ml), acidified with concentrated hydrochloric acid and extracted with chloroform. The chloroform solution is washed with small amounts of brine, dried, evaporated and purified by preparative thin-layer chromatography (as in Example 1D) to isolate 253 mg of 12β-(acetyloxy)-(3β,5β)-3-[[5-[4-(acetyloxy)phenyl]-3-(carboxymethyl)-1-oxopentyl]-oxy]card-20(22)-enolide.

(E) (3β,5β,12β)-3-[[3-(Carboxymethyl)-5-(4-hydroxyphenyl)-1-oxopentyl]oxy]-12,14-dihydroxycard-20(22)-enolide A solution of 12β-(acetyloxy)-(3β,5β)-3-[[5-[4-(acetyloxy)phenyl]-3-(carboxymethyl)-1-oxopentyl]oxy]card-20(22)-enolide (230 mg) in a mixture of methanol (10 ml) and water (2.5 ml) containing potassium carbonate (210 mg) is stirred at 10° to 15° C. for 2.5 hours. It is then acidified with concentrated hydrochloric acid. Isolation and purification of the product as described in Example 1E yields 44 mg of (3β,5β,12β)-3-[[3-(carboxymethyl)-5-(4-hydroxyphenyl)-1-oxopentyl]oxy]-12,14-dihydroxycard-20(22)-enolide, melting point at 126°–134° C.

EXAMPLE 4

(3β,5β,12β)-3-[[3-(Carboxymethyl)-6-(4-hydroxyphenyl)-1-oxohexyl]oxy]-12,14-dihydroxycard-20(22)-enolide (A) 3-[3-(4-Methoxyphenyl)propyl]glutaric acid 4-(4-Methoxyphenyl)butyraldehyde (5.34 g) is reacted with cyanoacetic acid (5.15 g) and sodium hydroxide (2.74 g) in a mixture of glyme (50 ml) and water (60 ml). The mixture is treated with hydrochloric acid and processed as described in Example 2A to afford the title compound (2.1 g) which on crystallization from ethyl acetate-chloroform-hexane had a melting point of 71°–73° C.

(B) 3-[3-(4-Hydroxyphenyl)propyl]glutaric acid

3-[3-(4-Methoxyphenyl)propyl]glutaric acid (2.0 g) is demethylated by the procedure described in Example 1B to afford, after crystallization of the product from ethyl acetate-chloroform-hexane, 1.2 g of 3-[3-(4-hydroxyphenyl)-propyl]glutaric acid, melting point 107°–108° C.

(C) 3-[3-(4-(Acetyloxy)phenyl]propyl]glutaric anhydride

3-[3-(4-Hydroxyphenyl)propyl]glutaric acid (533 mg) is reacted with acetic anhydride as described in Example 1C to afford 3-[3-[4-(acetyloxy)phenyl]propyl]glutaric anhydride, melting point 55°–57° C.

(D) 12$\beta$-(Acetyloxy)-(3$\beta$,5$\beta$)-3-[[6-[4-(acetyloxy)phenyl]-3-(carboxymethyl)-1-oxohexyl]oxy]card-20(22)-enolide A mixture of digoxigenin-12-acetate (216 mg) and 3-[[3-(4acetyloxy)phenyl]propyl]glutaric anhydride (610 mg) in dry pyridine (9.0 ml) is reacted for 18 hours and the product is isolated and purified as described in Example 1D to afford 245 mg of 12$\beta$-(acetyloxy)-(3$\beta$,5$\beta$)-3-[[6-[4-(acetyloxy)phenyl]-3-(carboxymethyl)-1-oxohexyl]oxy]card-20(22)-enolide, melting point 98°–113° C.

(E) (3$\beta$,5$\beta$,12$\beta$)-3-[[3-(Carboxymethyl)-6-(4-hydroxyphenyl)-1-oxohexyl]oxy]-12,14-dihydroxycard-20(22)-enolide A mixture of 12$\beta$-(acetyloxy) (3$\beta$,5$\beta$)-3-[[6-[4-(acetyloxy)phenyl]-3-(carboxymethyl)-1-oxohexyl]oxy]card-20(22)-enolide (150 mg) and potassium carbonate (172 mg) is reacted in a mixture of methanol (5.0 ml) and water (2 ml). The mixture is processed and purified as described in Example 1E to afford 58 mg of (3$\beta$,5$\beta$,12$\beta$)-3-[[3-(carboxymethyl-6-(4-hydroxyphenyl)-1-oxohexyl]oxy]-12,14-dihydroxycard-20(22)-enolide, melting point 115°–128° C.

EXAMPLE 5

(3$\beta$,5$\beta$,12$\beta$)-3-[[3-(Carboxymethyl)-7-(4-hydroxypheyl)-1-oxoheptyl]oxy]-12,14-dihydroxycard-20(22)-enolide Following the procedure of Example 4, but substituting 5-(4-methoxyphenyl)valeraldehyde for 4-(4-methoxyphenyl)-butyraldehyde yields the title compound.

DETAILED PROCEDURE FOR RADIOIODINATION OF DIGOXIGENIN DERIVATIVES

Sodium radioiodide (I$^{125}$) aqueous solution (10 ml; approximately 6 mCi) is added to a reaction vial containing a methanolic solution of (3$\beta$,5$\beta$,12$\beta$)-3-[4-carboxy-3-(4-hydroxyphenyl)-1-oxobutoxy]-12,14-dihydroxycard-20(22)-enolide (10 ml; 1 mg/ml). The vial is stoppered and a chloramine T solution (25 ml; 2 mg/ml in 0.5 M phosphate buffer, pH 7.5) is injected through the stopper. The vial is mixed well by shaking and allowed to stand for five minutes. Sodium metabisulfite solution (20 ml; 3 mg/ml in 0.5 M phosphate buffer, ph 7.5) is injected through the stopper to quench the reaction.

The reaction mixture is applied to a 40 ml Sephadex G-10 column and eluted with tris acetate buffer (0.05 M, pH 6.5). Forty-four drops per tube are collected with the aid of a fraction collector. Free iodide comes off around tube #38 and the iodinated product elutes off in two fractions, tubes 110 thru 130 (fraction I) and tubes 131 thru 150 (fraction II). Fraction II is found to be superior and is used in radioimmunoassays.

EXAMPLE 6

21-[4-Carboxy-3-(4-hydroxyphenyl)-1-oxobutoxy-11$\beta$,18-epoxy-18-hydroxypregn-4-ene-3,20-dione (A) 21-[3-(4-Acetyloxphenyl)-4-carboxy-1-oxobutoxy]-11$\beta$,18-epoxy-18-hydroxypregn-4-ene-3,20-dione Aldosterone (100 mg) is refluxed in dry pyridine (6.0 ml) with 3-(4-acetyloxyphenyl)glutaric anhydride (300 mg) for 2.0 hours. The solution is then cooled to room temperature, water is added and after standing for a few minutes evaporated in vacuo. The residue is dissolved in ethyl acetate (20 ml), washed with 15% hydrochloric acid (6.0 ml) and brine, dried and evaporated to afford 408 mg of a gum. A thin-layer chromatography examination of this material shows the presence of three steroidal products. It is then subjected to preparative thin-layer chromatography on two 2.0 mm silica gel plates (with two developments of the plates with chloroform-methanol (9:1) to isolate 135 mg of the title compound, melting point 145°–160° C. with consistent spectral data.

(B) 21-[4-Carboxy-3-(4-hydroxyphenyl)-1-oxobutoxy]-11$\beta$,18-epoxy-18-hydroxypregn-4-ene-3,20-dione A solution of 21-[3-(4-acetyloxyphenyl)-4-carboxy-1-oxobutoxy]-11$\beta$,18-epoxy-18-hydroxypregn-4-ene,3,20-dione (130 mg) in anhydrous methanol (15 ml) containing triethylamine (0.2 ml) is allowed to stand at room temperature for 24 hours. The methanol is then evaporated in vacuo, the residue is diluted with water (5.0 ml), acidified with 10% hydrochloric acid and extracted with ethyl acetate (three 5.0 ml portions). The ethyl acetate solution is washed with brine, dried over anhydrous magnesium sulfate, evaporated and the residue is subjected to preparative thin-layer chromatography on silica gel plates (using chloroform-methanol, 9:1 for development) to isolate 83 mg of the title compound, melting point 145°–152° C., with consistent spectral data.

DETAILED PROCEDURE FOR RADIOIODINATION OF ALDOSTERONE DERIVATIVE

To a solution of 21-[4-Carboxy-3-(4-hydroxyphenyl)-1-oxobutoxy]-11$\beta$,18-epoxy-18-hydroxypregn-4-ene-3,20-dione (5.0 $\mu$g) in dioxane-0.5 M borate buffer (1:9, 50 $\mu$l) at pH 8.5 are added successively 20 $\mu$l of aqueous solutions of sodium radioiodide (I$^{125}$, 4 mCi) and freshly prepared chloramine-T (80 $\mu$g). After 90 seconds, the reaction is stopped by the addition of sodium bisulfite (80 $\mu$g) in water (20 $\mu$l). The solution is applied on a 5×20 cm silica gel plate which is developed with chloroform-methanol (9:1). The band of radioiodinated product is located using a scanner and is isolated by extraction with ethanol. The concentrated ethanol solution is stored at 15° C.

EXAMPLE 7

21-[4-Carboxy-3-(4-hydroxyphenyl)-1-oxobutoxy]-11β,17-dihydroxypregn-4-ene-3,20-dione (A) 21-[3-(4-Acetyloxyphenyl)-4-carboxy-1-oxobutoxy]-11β,17-dihydroxypregn-4-ene-3,20-dione A solution of cortisol (346 mg) and 3-(4-acetyloxyphenyl)glutaric anhydride (496 mg) in dry pyridine (5.0 ml) is refluxed for 40 minutes. The pyridine is evaporated in vacuo, the residue is diluted with ethyl acetate (30 ml), washed with 15% hydrochloric acid (10 ml) and brine, dried over anhydrous magnesium sulfate and evaporated to yield 840 mg of a powder. Examination of the NMR spectrum and TLC behavior of this material shows that it is a 1:1 mixture of the title compound and 3-(4-acetyloxypheyl)glutaric acid.

(B) 21-[4-Carboxy-3-(4-hydroxyphenyl)1-oxobutoxy]-11β,17-dihydroxypregn-4-ene-3,20dione The mixture obtained above (700 mg) is dissolved in anhydrous methanol (30 ml) containing triethylamine (1.0 ml) and the solution is refluxed for 5.0 hours. The solution is cooled, acidified with 10% hydrochloric acid and most of the methanol is evaporated in vacuo. The resulting slurry is extracted with ethyl acetate, the ethyl acetate solution is washed with brine, dried and evaporated. The residue is subjected to preparative thin-layer chromatography on two 2.0 mm silica gel plates using chloroform-methanol (9:1) for development and the major band is isolated with chloroform-methanol (8:2) to afford 300 mg of the title compound, melting point 98°-110° C.

DESCRIPTION FOR RADIODINATION OF CORTISOL DERIVATIVE

21-[4-Carboxy-3-(4-hydroxyphenyl)-1-oxobutoxy]-11β,17-dihydroxypregn-4-ene-3,20-dione is radiolabeled with $I^{125}$ using the procedure described above for the radioiodination of aldosterone derivatives.

EXAMPLE 8

(3β,5β,12β)-3-[4-Carboxy-3-(4-hydroxy-3-methylpheyl)-1-oxobutoxy]-12,14-dihydroxycard-20(22)-enolide (A) 3-(Methoxy-3-methylphenyl)glutaric acid A mixture of 4-methoxy-3-methylbenzaldehyde (100 mmole), cyanoacetic acid (210 mmole) and potassium hydroxide (250 mmole) in water (500 ml) is stirred at room temperature for 20 hours. The resulting solution is acidified with concentrated hydrochloric acid (100 ml) and the mixture is refluxed for 60 hours. After cooling, it is saturated with sodium chloride and extracted with ethyl acetate to afford the title compound.

(B) 3-(4-Hydroxy-3-methylphenyl)glutaric acid

Following the procedure described in Example 1B, but substituting 3-(4-methoxy-3-methylphenyl)glutaric acid for 3-(4-methoxyphenyl)glutaric acid, yields the title compound.

(C) 3-[4-(Acetyloxy)-3-methylphenyl)]glutaric anhydride

Following the procedure described in Example 1C, but substituting 3-(4-hydroxy-3-methylphenyl)glutaric acid for 3-(4-hydroxyphenyl)glutaric acid, yields the title compound.

(D) 12β-(Acetyloxy)-(3β,5β)-3-[4-carboxy-3-[4-(acetyloxy)-3-methylphenyl]-1-oxobutoxy]-14-hydroxycard-20(22)-enolide Following the procedure described in Example 1D, but substituting 3-[4-(acetyloxy)-3-methylphenyl)]glutaric anhydride for 3-(4-acetyloxyphenyl)glutaric anhydride, yields the title compound.

(E) (3β,5β,12β)-3-[4-Carboxy-3-[(4-hydroxy-3-methylphenyl]-1-oxobutoxy]-12,14-dihydroxycard-20(22)-enolide Following the procedure described in Example 1E, but substituting 12β-(acetyloxy)-(3β,5β)-3-[4-carboxy-3-[4-(acetyloxy)-3-methylphenyl]-1-oxobutoxy]-14-hydroxycard-20(22)-enolide for 12β-(acetyloxy)-(3β,5β)-3-[4-carboxy-3-[4-(acetyloxy)phenyl]-1-oxobutoxy-14-hydroxycard-20(22)-enolide, yields the title compound.

EXAMPLES 9-26

Following the procedure described in Example 6, but substituting the steroid listed in Column I for aldosterone and the anhydride reagent listed in Column II for 3-(4-acetyloxyphenyl)glutaric anhydride, yields the product listed in Column III.

| Column I | Column II | Column III |
| --- | --- | --- |
| (9) cholesterol | 3-(4-acetyloxyphenyl) glutaric anhydride | 3β-[4-carboxy-3-(4-hydroxyphenyl)-1-oxobutoxy]-cholest-5-ene |
| (10) cortisone | 3-(4-acetyloxyphenyl) glutaric anhydride | 21-[4-carboxy-3-(4-hydroxyphenyl)-1-oxobutoxy]-17-hydroxypregn-4-ene-3,11,20-trione |
| (11) corticosterone | 3-[(4-acetyloxy)-3-methylphenyl]glutaric anhydride | 21-[(4-acetyloxy-3-(4-hydroxy-3-methylphenyl)-1-oxobutoxy]-11β-hydroxypregn-4-ene-3,20-dione |
| (12) prednisolone | 3-(4-acetyloxyphenyl) glutaric anhydride | 21-[4-carboxy-3-(4-hydroxyphenyl)-1-oxobutoxy]-11β,17-dihydroxypregna-1,4-diene-3,20-dione |
| (13) methylprednisolone | 3-(4-acetyloxyphenyl) glutaric anhydride | 21-[4-carboxy-3-(4-hydroxyphenyl)-1-oxobutoxy]-11β,17-dihydroxy-6α-methylpregna-1,4-diene-3,20-dione |
| (14) triamcinolone | 3-(4-acetyloxyphenyl) glutaric anhydride | 21-[4-carboxy-3-(4-hydroxyphenyl)-1-oxobutoxy]-9-fluoro-11β,16β,17-trihydroxypregna-1,4-diene-3,20-dione |
| (15) betamethasone | 3-(4-acetyloxyphenyl) glutaric anhydride | 21-[4-carboxy-3-(4-hydroxyphenyl)-1-oxobutoxy]-9-fluoro-11β,17-dihydroxy-16β-methylpregna-1,4-diene-3,20-dione |
| (16) dexamethasone | 3-(4-acetyloxyphenyl) glutaric anhydride | 21-[4-carboxy-3-(4-hydroxyphenyl)-1-oxobutoxy]-9-fluoro-11β,17-dihydroxy-16α-methylpregna-1,4-diene-3,20-dione |
| (17) triamcinolone acetonide | 3-[4-(acetyloxyphenyl) methyl]glutaric anhydride | 21-[4-carboxy-3-[(4-hydroxyphenyl)methyl]-1-oxobutoxy]-9-fluoro-11β,16β,17-trihydroxypregna-1,4-diene-3,20-dione, 16,17-acetonide |
| (18) betamethasone valerate | 3-(4-acetyloxyphenyl) glutaric anhydride | 21-[4-carboxy-3-(4-hydroxyphenyl)-1-oxobutoxy]-9-fluoro-11β-hydroxy-16β-methyl-17-(1-oxopentyl- |

-continued

| | Column I | Column II | Column III |
|---|---|---|---|
| (19) | halcinonide | 3-(4-acetyloxyphenyl) glutaric anhydride | oxy)pregna-1,4-diene-3,20-dione 11β-[4-carboxy-3-(4-hydroxyphenyl)-1-oxobutoxy]-21-chloro-9-fluoro-16β,17-dihydroxypregna-1,4-diene-3,20-dione, 16,17-acetonide |
| (20) | estrone | 3-(4-acetyloxyphenyl) glutaric anhydride | 3-[4-carboxy-3-(4-hydroxxyphenyl)-1-oxobutoxy]-estra-1,3,5(10)-triene-17-one |
| (21) | estradiol | 3-[[(4-acetyloxy)phenyl]-methyl]glutaric anhydride | 17β-[4-carboxy-3-[(4-hydroxyphenyl)methyl]-1-oxo-butoxy]estra-1,3,5(10)-triene-3-ol |
| (22) | estriol | 3-(4-acetyloxyphenyl) glutaric anhydride | 3-[4-carboxy-3-(4-hydroxyphenyl)-1-oxo-butoxy]estra-1,3,5(10)-triene-16α,17β-diol |
| (23) | testosterone | 3-[4-(acetyloxy)-3-methyl-phenyl]glutaric anhydride | 17β-[4-carboxy-3-(4-hydroxy-3-methylphenyl)-1-oxobutoxy]androsta-4-ene-3-one |
| (24) | 19-nortestosterone | 3-(4-acetyloxyphenyl) glutaric anhydride | 17β-[4-carboxy-3-(4-hydroxyphenyl)-1-oxobutoxy]-19-norandrosta-4-en-3-one |
| (25) | methyltestosterone | 3-(4-acetyloxyphenyl) glutaric anhydride | 17β-[4-carboxy-3-(4-hydroxyphenyl)-1-oxobutoxy]-17α-methylandrosta-4-en-3-one |
| (26) | pregnenolone | 3-[(4-acetyloxyphenyl)ethyl] glutaric anhydride | 3β-[[3-(carboxymethyl)-5-(4-hydroxyphenyl)-1-oxopentyl]oxy]pregn-5-ene-20-one |
| (27) | 11α-hydroxyprogesterone | 3-[4-(acetyloxy)phenyl]glutaric anhydride | 11α-[4-carboxy-3-(4-hydroxyphenyl)-1-oxobutoxy]-pregn-4-ene-3,20-dione |

What is claimed is:

1. A compound having the formula

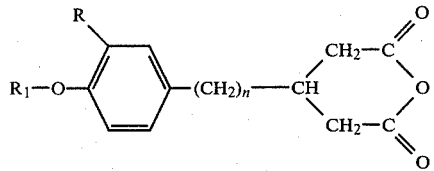

wherein R is hydrogen or an alkyl group having 1 to 3 carbon atoms; $R_1$ is alkanoyl having 2 to 6 carbon atoms an n is 0, 1, 2, 3 or 4.

2. A compound in accordance with claim 1 wherein $R_1$ is acetyl and R is hydrogen.

3. A compound in accordance with claim 1 wherein n is 0.

4. A compound in accordance with claim 1 wherein n is 1.

5. A compound in accordance with claim 1 wherein n is 2.

6. A compound in accordance with claim 1 wherein n is 3.

7. A compound in accordance with claim 1 wherein n is 4.

* * * * *

UNITED STATES PATENT OFFICE
CERTIFICATE OF CORRECTION

Patent No. 4,221,725  Dated September 9, 1980

Inventor(s) Jack Bernstein, et al

It is certified that error appears in the above-identified patent and that said Letters Patent are hereby corrected as shown below:

On the title page after "Jack Bernstein", "News Brunswick" should read --New Brunswick--

Column 6, line 1, the "D)" is missing as part of the Example.

Column 7, line 5, "pheyl]" should read --phenyl]--

Column 7, line 7, insert a ")" after "mg"

Column 7, line 17, "pheyl]" should read --phenyl]--

Column 9, line 44 "pheyl)" should read --phenyl)--

Column 9, line 64, "ph" should read --pH--

Column 11, line 16, "acetyloxypheyl)" should read --acetyloxyphenyl)--

Column 11, line 18, insert a hyphen (-) after "20"

Claim 1, column 14, line 23, "an" should read --and--

Signed and Sealed this

Thirteenth Day of January 1981

[SEAL]

Attest:

SIDNEY A. DIAMOND

Attesting Officer  Commissioner of Patents and Trademarks